United States Patent
Spadgenske

(10) Patent No.: US 10,256,590 B2
(45) Date of Patent: *Apr. 9, 2019

(54) INTERCONNECT FOR IMPLANTABLE MEDICAL DEVICE HEADER

(71) Applicant: Cardiac Pacemakers, Inc., St. Paul, MN (US)

(72) Inventor: Scott A. Spadgenske, Buffalo, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 42 days.

This patent is subject to a terminal disclaimer.

(21) Appl. No.: 15/480,480

(22) Filed: Apr. 6, 2017

(65) Prior Publication Data

US 2017/0279238 A1 Sep. 28, 2017

Related U.S. Application Data

(63) Continuation of application No. 15/058,820, filed on Mar. 2, 2016, now Pat. No. 9,620,918, which is a continuation of application No. 11/860,364, filed on Sep. 24, 2007, now Pat. No. 9,289,615, which is a continuation of application No. 10/320,044, filed on Dec. 16, 2002, now Pat. No. 7,274,963.

(51) Int. Cl.
| | |
|---|---|
| *A61N 1/375* | (2006.01) |
| *H01R 43/00* | (2006.01) |
| *H01R 13/504* | (2006.01) |
| *H01R 43/16* | (2006.01) |
| *H01R 43/18* | (2006.01) |

(52) U.S. Cl.
CPC ......... *H01R 43/005* (2013.01); *A61N 1/3752* (2013.01); *A61N 1/3754* (2013.01); *H01R 13/504* (2013.01); *H01R 43/16* (2013.01); *H01R 43/18* (2013.01); *Y10S 439/909* (2013.01)

(58) Field of Classification Search
CPC .. A61N 1/3752; A61N 1/3754; H01R 13/504; Y10S 439/909
See application file for complete search history.

(56) References Cited

U.S. PATENT DOCUMENTS

| | | |
|---|---|---|
| 4,041,956 A | 8/1977 | Purdy et al. |
| 4,142,532 A | 3/1979 | Ware |
| 4,182,345 A | 1/1980 | Grose |

(Continued)

OTHER PUBLICATIONS

"U.S. Appl. No. 10/320,044, Non-Final Office Action dated Dec. 1, 2006", 12 pgs.

(Continued)

*Primary Examiner* — Tammie K Marlen
(74) *Attorney, Agent, or Firm* — Schwegman Lundberg & Woessner, P.A.

(57) ABSTRACT

A modular header and method of fabricating same for making electrical connection between an array of feedthrough pins extending through a wall of a hermetically sealed enclosure of an implantable medical device and lead connect or receptacles within the header in which the header is fabricated using a pre-formed molded header module, together with a set or harness of interconnected flexible conductors incorporated and sealed by an overlayer of medical grade polymer material. The assembled modular header is capable of complete pre-testing prior to assembly onto an implantable medical device.

10 Claims, 8 Drawing Sheets

(56) References Cited

U.S. PATENT DOCUMENTS

| | | | |
|---|---|---|---|
| 4,262,673 | A | 4/1981 | Kinney et al. |
| 5,067,903 | A | 11/1991 | Szyszkowski |
| 5,070,605 | A | 12/1991 | Daglow et al. |
| 5,235,742 | A | 8/1993 | Szyszkowski |
| 5,282,841 | A | 2/1994 | Szyszkowski |
| 5,336,246 | A | 8/1994 | Dantanarayana |
| 5,431,695 | A | 7/1995 | Wiklund et al. |
| 5,456,698 | A | 10/1995 | Byland et al. |
| 5,522,861 | A | 6/1996 | Sikorski et al. |
| 5,535,097 | A | 7/1996 | Ruben et al. |
| 5,851,221 | A | 12/1998 | Rieder et al. |
| 5,899,930 | A | 5/1999 | Flynn et al. |
| 5,906,634 | A | 5/1999 | Flynn et al. |
| 6,205,358 | B1 | 3/2001 | Haeg et al. |
| 6,792,312 | B2 | 9/2004 | Bruchmann et al. |
| 6,817,905 | B2 | 11/2004 | Zart et al. |
| 6,884,122 | B2 | 4/2005 | Robinson et al. |
| 7,274,963 | B2 | 9/2007 | Spadgenske |
| 9,289,615 | B2 | 3/2016 | Spadgenske et al. |
| 9,620,918 | B2 | 4/2017 | Spadgenske |
| 2002/0107555 | A1 | 8/2002 | Rusin et al. |
| 2004/0116976 | A1 | 6/2004 | Spadgenske |
| 2008/0009912 | A1 | 1/2008 | Spadgenske |
| 2010/0285697 | A1 | 11/2010 | Zart et al. |
| 2016/0181754 | A1 | 6/2016 | Spadgenske |

OTHER PUBLICATIONS

"U.S. Appl. No. 10/320,044, Advisory Action dated Apr. 24, 2006", 3 pgs.
"U.S. Appl. No. 10/320,044, Amendment filed Mar. 1, 2007 in Response to Non-Final Office Action dated Dec. 1, 2006", 10 pgs.
"U.S. Appl. No. 10/320,044, Amendment filed Apr. 7, 2006 in Response to Final Office Action dated Feb. 9, 2006", 11 pgs.
"U.S. Appl. No. 10/320,044, Amendment filed Oct. 2, 2006 in Response to Non-Final Office Action dated Jul. 26, 2006", 13 pgs.
"U.S. Appl. No. 10/320,044, Amendment filed Dec. 8, 2005 in Response to Non-Final Office Action dated Sep. 9, 2005", 16 pgs.
"U.S. Appl. No. 10/320,044, Final Office Action dated Feb. 9, 2006", 8 pgs.
"U.S. Appl. No. 10/320,044, Non-Final Office Action dated Jul. 26, 2006", 7 pgs.
"U.S. Appl. No. 10/320,044, Non-Final Office Action dated Sep. 9, 2005", 8 pgs.
"U.S. Appl. No. 10/320,044, Notice of Allowance dated May 21, 2007", 4 pgs.
"U.S. Appl. No. 11/860,364, Advisory Action dated Feb. 15, 2011", 3 pgs.
"U.S. Appl. No. 11/860,364, Advisory Action dated Jul. 15, 2014", 3 pgs.
"U.S. Appl. No. 11/860,364, Examiner Interview Summary dated Feb. 8, 2011", 4 pgs.
"U.S. Appl. No. 11/860,364, Examiner Interview Summary dated Aug. 24, 2010", 3 pgs.
"U.S. Appl. No. 11/860,364, Final Office Action dated Jan. 28, 2014", 9 pgs.
"U.S. Appl. No. 11/860,364, Final Office Action dated Jun. 11, 2015", 11 pgs.
"U.S. Appl. No. 11/860,364, Final Office Action dated Nov. 24, 2010", 13 pgs.
"U.S. Appl. No. 11/860,364, Non Final Office Action dated Jan. 9, 2015", 10 pgs.
"U.S. Appl. No. 11/860,364, Non Final Office Action dated May 24, 2013", 12 pgs.
"U.S. Appl. No. 11/860,364, Non-Final Office Action dated May 14, 2010", 9 pgs.
"U.S. Appl. No. 11/860,364, Notice of Allowance dated Nov. 16, 2015", 15 pgs.
"U.S. Appl. No. 11/860,364, Response filed Jan. 31, 2011 to Final Office Action dated Nov. 24, 2010", 13 pgs.
"U.S. Appl. No. 11/860,364, Response filed Feb. 5, 2010 to Restriction Requirement dated Jan. 15, 2010", 9 pgs.
"U.S. Appl. No. 11/860,364, Response filed Mar. 9, 2011 to Final Office Action dated Nov. 24, 2010", 15 pgs.
"U.S. Appl. No. 11/860,364, Response filed Apr. 9, 2015 to Non Final Office Action dated Jan. 9, 2015", 10 pgs.
"U.S. Appl. No. 11/860,364, Response filed Jun. 30, 2014 to Final Office Action dated Jan. 28, 2014", 10 pgs.
"U.S. Appl. No. 11/860,364, Response filed Sep. 9, 2015 to Final Office Action dated Jun. 11, 2015", 10 pgs.
"U.S. Appl. No. 11/860,364, Response filed Sep. 14, 2010 to Non Final Office Action dated May 14, 2010", 14 pgs.
"U.S. Appl. No. 11/860,364, Response filed Oct. 2, 2009 to Restriction Requirement dated Sep. 2, 2009", 10 pgs.
"U.S. Appl. No. 11/860,364, Response filed Nov. 21, 2013 to Non Final Office Action dated May 24, 2013", 10 pgs.
"U.S. Appl. No. 11/860,364, Restriction Requirement dated Jan. 15, 2010", 7 pgs.
"U.S. Appl. No. 11/860,364, Restriction Requirement dated Sep. 2, 2009", 7 pgs.

INTERCONNECT FOR IMPLANTABLE MEDICAL DEVICE HEADER

CROSS-REFERENCE TO RELATED APPLICATIONS

This patent application is a continuation of U.S. patent application Ser. No. 15/058,820 entitled "INTERCONNECT FOR IMPLANTABLE MEDICAL DEVICE HEADER," filed on Mar. 2, 2016, now issued as U.S. Pat. No. 9,620,918, which is a continuation of U.S. patent application Ser. No. 11/860,364 entitled "INTERCONNECT FOR IMPLANTABLE MEDICAL DEVICE HEADER," filed on Sep. 24, 2007, now issued as U.S. Pat. No. 9,289,615, which is a continuation of U.S. patent application Ser. No. 10/320,044, now issued as U.S. Pat. No. 7,274,963, entitled "INTERCONNECT FOR IMPLANTABLE MEDICAL DEVICE HEADER," filed on Dec. 16, 2002 by Spadgenske and assigned to Cardiac Pacemakers, Inc., the disclosure of each of which is incorporated herein by reference.

BACKGROUND OF THE INVENTION

I. Field of the Invention

The present invention relates generally to implantable medical devices having external electrical connections and electrical feed-throughs and, more particularly, to the provision of a pre-built modular sub-assembly interconnect system for a header module such as are found in implantable pulse generators (IPG's) associated with cardiac rhythm management and other hermetically sealed implantable medical devices.

II. Related Art

Implantable medical devices of a class having electrical circuit components are well known in the medical field. These include cardiac rhythm management devices which commonly include a pacemaker unit which, in turn, includes sensing and control circuitry, together with a power supply, protectively housed in a hermetically sealed case or can in combination with one or more conductive electrical leads designed to connect to the patient's heart muscle tissue, the activity of which is to be sensed and stimulated. To maintain the integrity of the components in the sealed case, provision must be made for hermetically sealed passage of electrical conductors to the exterior for connection to the leads and ultimately to tissue of interest. This has been typically accomplished by using connector blocks and associated feed-through conductors located external to the IPG housing which, themselves, are typically placed within a sealed header structure of medical grade polymer material.

While great strides have been made in improving the sophistication of the pacemaker devices themselves, the assembly and testing of the devices has remained relatively dependent on the skill of the assembly workers. Attempts have been made in the art to simplify the assembly process and to improve the acceptance rate of completed devices which undergo rigorous testing once assembled. In U.S. Pat. No. 5,282,841, for example, a ribbon conductor set or harness is provided to facilitate connection of feed-through terminal conductors to corresponding connector blocks in the header in which the individual ribbon conductors leads can be shaped to a three-dimensional geometry for ease of assembly. The assembled or fully interconnected unit is thereafter subjected to an over molding or coating step in which an entire epoxy head is cast over the assembly to encapsulate and seal the connecting components. That system, however, still depends on the skill of workers for assembly and requires extensive over molding. Furthermore, the electrical integrity of the unit cannot be tested until it is completely assembled.

U.S. Pat. No. 6,205,358 B1 discloses a pre-formed header module in combination with a ribbon connector harness which is assembled and placed between feed-through pins on the side of the sealed enclosure and the header module and thereafter captured in an over molding or backfilling step using medical grade polymer. This system also suffers from similar drawbacks to those described above.

SUMMARY OF THE INVENTION

By means of the present invention there is provided a module header sub-assembly for assembly to in connection with a hermetically sealed implantable medical device which solves many of the above problems and overcomes the drawbacks of previous versions of such devices. The present invention provides the desired electrical feed-through, but, unlike previous header units, the header of the present invention is a sufficiently complete sub-assembly such that it can be tested for functional integrity prior to assembly onto the hermetically sealed medical device. The present header also facilitates assembly and reduces the amount of necessary backfill.

The modular header sub-assembly of the present invention eliminates the routing of individual feed-through wires to the respective connector blocks by providing an array of metallic conductors incorporated into the sub-assembly itself and molding in either the primary, secondary or even a tertiary mold operation. In this manner, one end of each of the flexed conductors is connected to the appropriate connector block and the other end aligned with the remaining traces to be connected to corresponding feed-through pins in the hermetically sealed IPG unit. In this manner, an array of aligned connectors is arranged to match an array of aligned feed-through pins such that connection between them can be made through a small window readily backfilled after connecting and welding operations. This enables additional site connectors to be implemented while maintaining and actually decreasing header size when compared to conventional wire routings. The flex or trace design further allows all weld locations to be in a minimal number of weld access planes and therefore readily adaptable to process automation. Furthermore, pre-fabricated wire terminations provide repeatable attached locations on conductor sites making feasible alternate welding techniques such as programmable micro-laser welding.

The reduction of the volume required to be backfilled after welding operations also eliminates concerns with respect to the sealing integrity of the backfill which is currently dependent on the technique and skill of the operator and the subsequent inspection. The pre-fabricated wire terminations further eliminates a major manufacturing step involved in routing and backfilling of the wire channels in the header and further allows testing of the integrity of each conductor in the header prior to assembly of the header to the hermetically sealed device. Since the flex/conductor system can be an integral part of the header, mold/sealing operations requiring high pressures are now possible since the header does not have to be connected to the device prior to these primary or secondary mold/seal operations.

DETAILED DESCRIPTION

It will be appreciated that the present invention enables the header to be built as a complete modular sub-assembly capable of being tested for circuit integrity prior to attachment to the feed-through pins of the hermetically sealed pacer, other IPG or other implanted unit. The present invention also greatly simplifies the connection process and reduces the amount of backfilling required to complete the header/hermetically sealed IPG assembly. While the detailed description which follows is limited to one or two embodiments, it will also be understood that these are intended as examples only and are not intended to limit the scope of the inventive concept in any manner.

Figure 1:
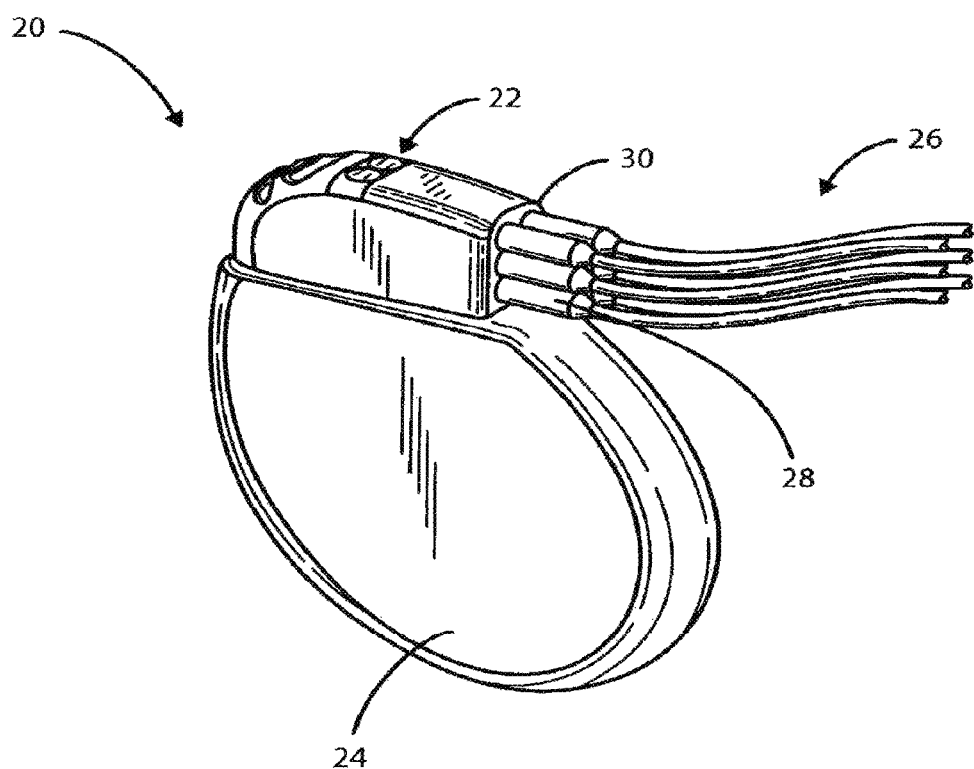
FIG. 1 is a schematic representation of an implantable medical device in the form of an IPG of a class suitable for including the header interconnect system of the present invention.

FIG. 1 depicts a simplified schematic view of an implantable medical device 20 of a class suitable for utilizing the header of the present invention including a pre-formed, pre-assembled header module 22 attached to a hermetically sealed enclosure 24. A plurality of leads 26, which typically includes atrial and ventricle pacing/sensing leads, for example, are connected to the header using elongated lead connectors 28 and receptacles as at 30. The leads are further connected to feed-throughs using feed-through pins extending through the hermetically sealed enclosure 24. These are beneath the backfilled surface and so are not shown in the figure.

Generally, the hermetically sealed enclosure 24 contains a power source in the form of an electrochemical cell which may be a lithium battery, control and sensing circuitry which controls the operation of the device and senses and records data according to programmed instructions which may be fixed or time-variable and microprocessor controlled. A telemetry transceiver system is provided to enable the device to communicate with an external programmer.

It will be appreciated that particular electronic features may vary considerably from device to device and the practice of the present invention is not dependent or based on any particular embodiment of such a unit, but is based on a common need for pass-through connections.

Figure 2A:
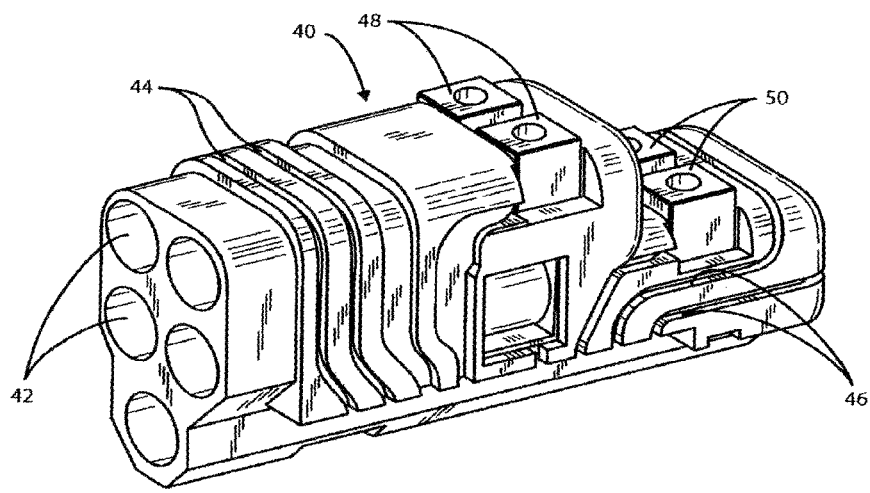
FIG. 2A is a greatly enlarged perspective view of a primary molding of a pre-formed header module showing pre-formed patterned conductor channels and including connector blocks adapted to receive a corresponding connected array system or harness of flexible connectors in accordance with the present invention.
Figure 2B:
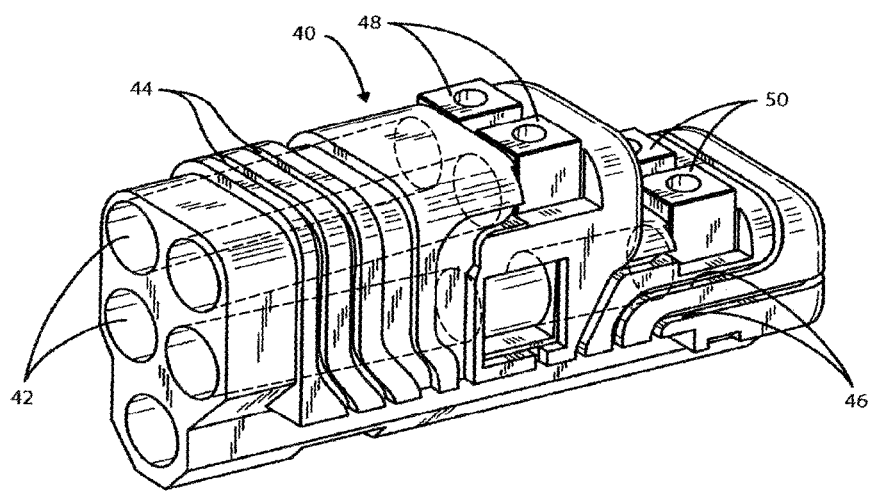
FIG. 2B is a perspective view of a header showing internal conductive paths in hidden lines.

FIGS. 2A and 2B is a greatly enlarged perspective view of a pre-formed molded header module 40 having a plurality of elongated external lead connector receptacles as at 42. The pre-formed primary header module is provided with a plurality of recessed conductor channels as at 44 and 46 which connect with corresponding connector blocks as at 48 and 50. The lead connector receptacles 42 also connect with corresponding connector blocks 48 and 50 through internal passages (not shown) in a well known manner.

Figure 3:
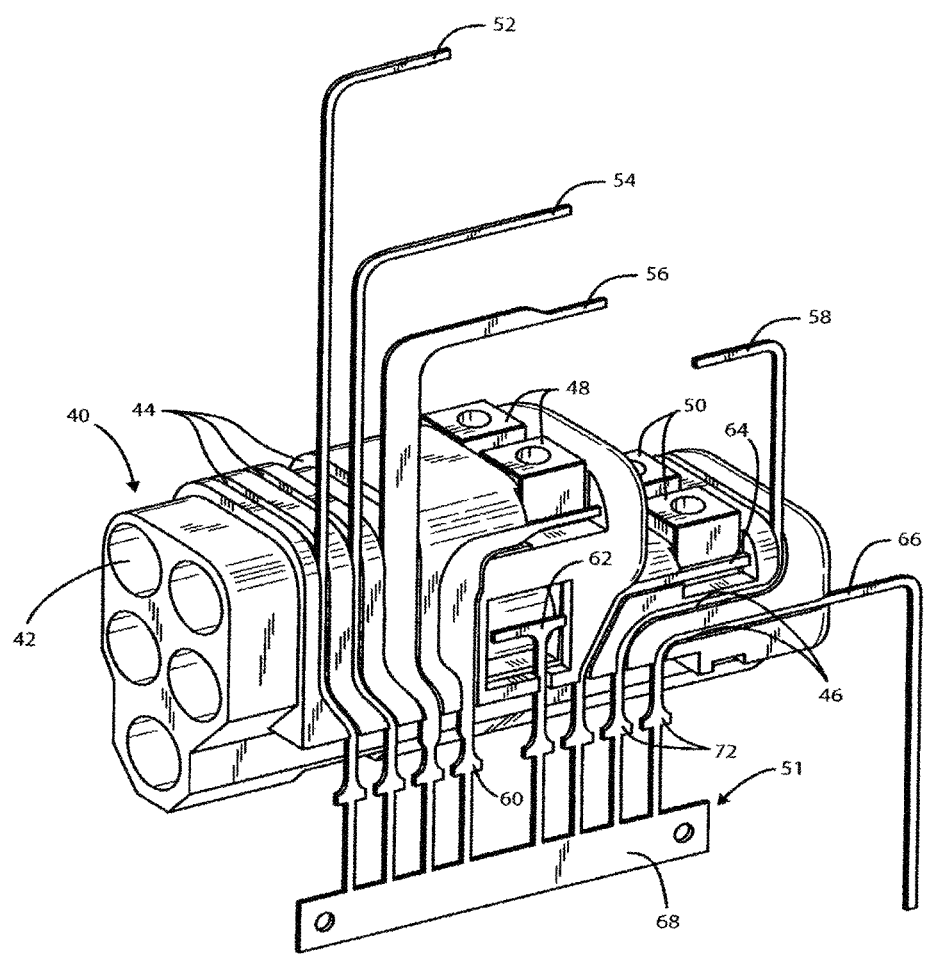
FIG. 3 is a perspective view similar to that of FIGS. 2A and 2B as it is being addressed and fitted with a pre-formed harness of flexible conductors in accordance with the invention.

As shown in FIG. 3, the pre-formed flex conductor system or harness 51 is provided with leads or conductors represented by even reference characters 52 through 66 configured to fit into the corresponding recessed channels 44, 46 and to have corresponding free ends designed to attach to corresponding connector block as at 48 or 50, or otherwise (not shown) each flexible connector further having a second end fixed in spaced relation along a removable common member 68 provided for production of the harness and ease of assembly onto the primary molded module 40.

Figure 4:
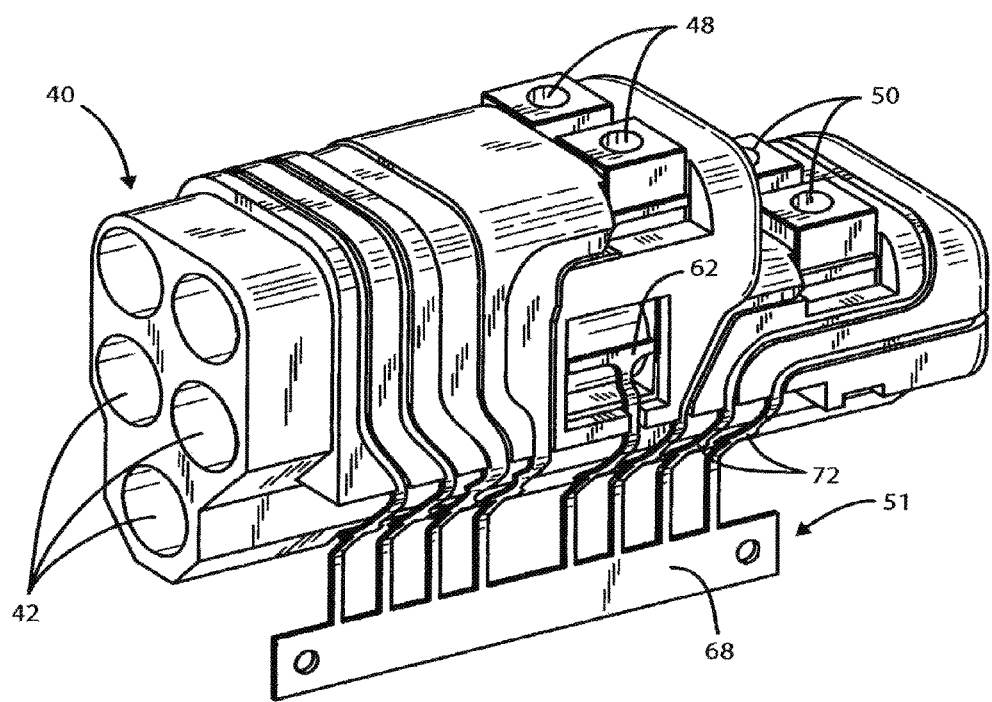
FIG. 4 depicts the pre-formed header module of FIGS. 2A, 2B and 3 with the connector system assembled in place.

FIG. 4 depicts the molded module 40 of FIGS. 2 and 3 with the flexible conductors, which may be constructed of a conducting foil, or the like, situated in place in the corresponding relevant receiving channels 44, 46. The material of the flexible conductors 52-66 is one easily deformed to fit the relevant recessed channel 44, 46 yet is sufficiently rugged to withstand the manufacture, assembly and a subsequent over-molding operation while remaining intact. The material conductive of the traces or harness is preferably a stainless steel, but other bio-compatible materials which adapt themselves to the manufacturing and assembly steps satisfactorily in accordance with the invention may be used.

Figure 5A:
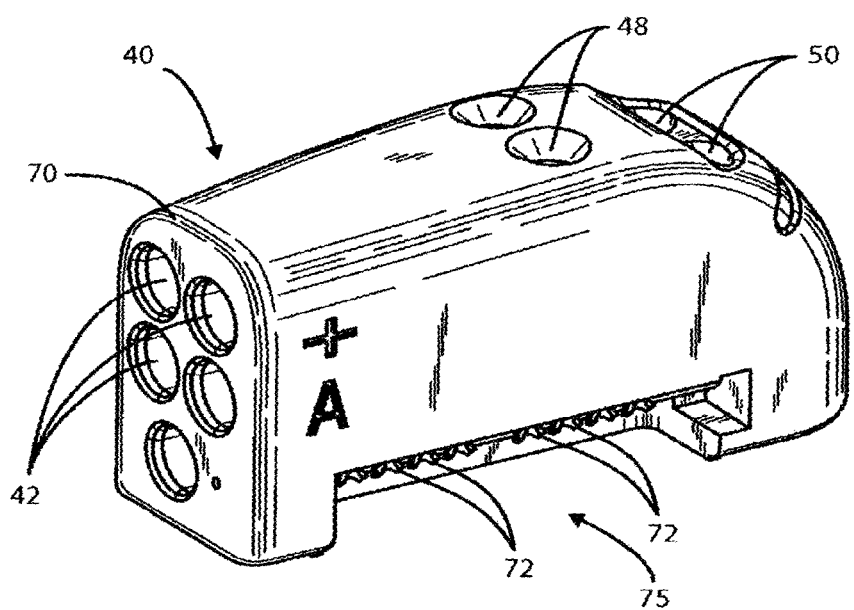
FIG. 5A is a view of the pre-formed header module of FIG. 4 after the application of a secondary overlayer of medical grade polymer.
Figure 5B:
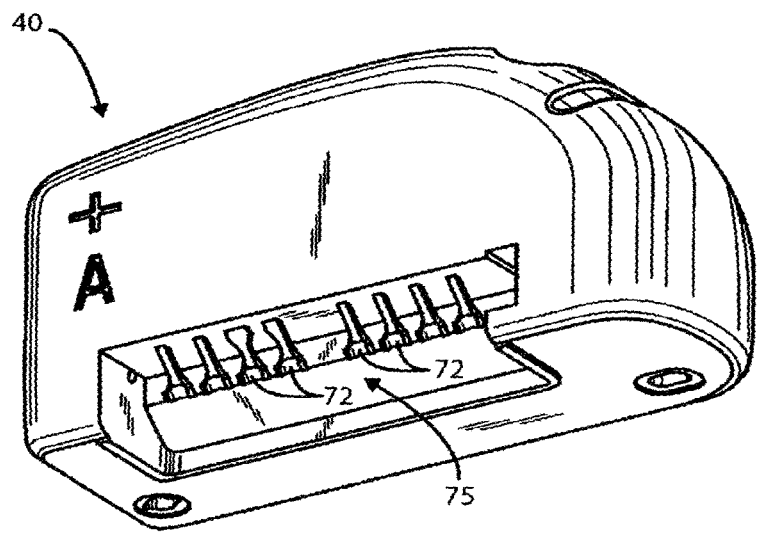
FIG. 5B is a view similar to FIG. 5A with the header module rotated to better depict the array of connecting terminals adapted to receive the feed-through pins of a corresponding hermetically sealed device.

FIGS. 5A and 5B illustrate the pre-molded or primary molded header modules 40 of FIGS. 2-4 after application and routing of the conductive traces in the channels 44, 46 and connection of them to the corresponding connector blocks, some of which are illustrated at 48 and 50, and after a secondary molding or first over-molding step has been performed and the common member 68 has been removed. The over-molding layer 70 seals the conductors within the modular header exposing only the external connection sites as at 42, 48 and 50 and an array of terminal spade connectors 72 adapted to be connected to corresponding feed-through pin 74 shown in FIG. 9. As shown particularly in the enlarged fragment views of FIG. 9, the spade connectors 72 can readily and automatically be crimped about feed-through pins 74 and the connection welded as at 76.

Figure 6:
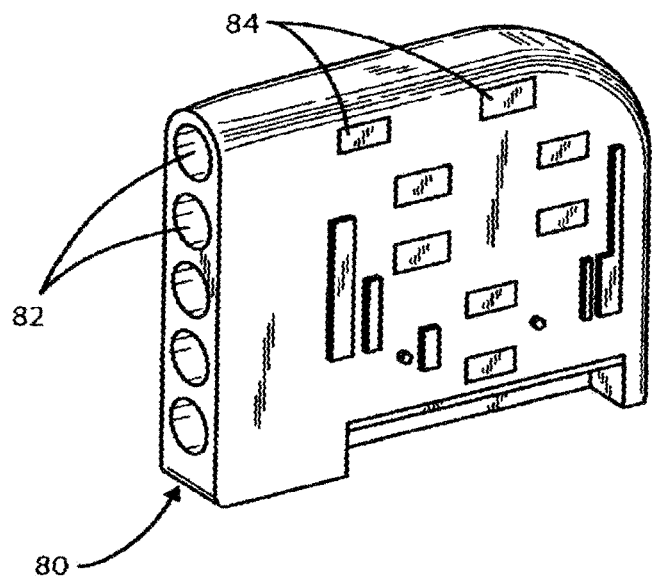
FIGS. 6-8 depict views of assembly steps characteristic of an alternative embodiment of an inline connector design using a side connection system in the modular header.
Figure 7:
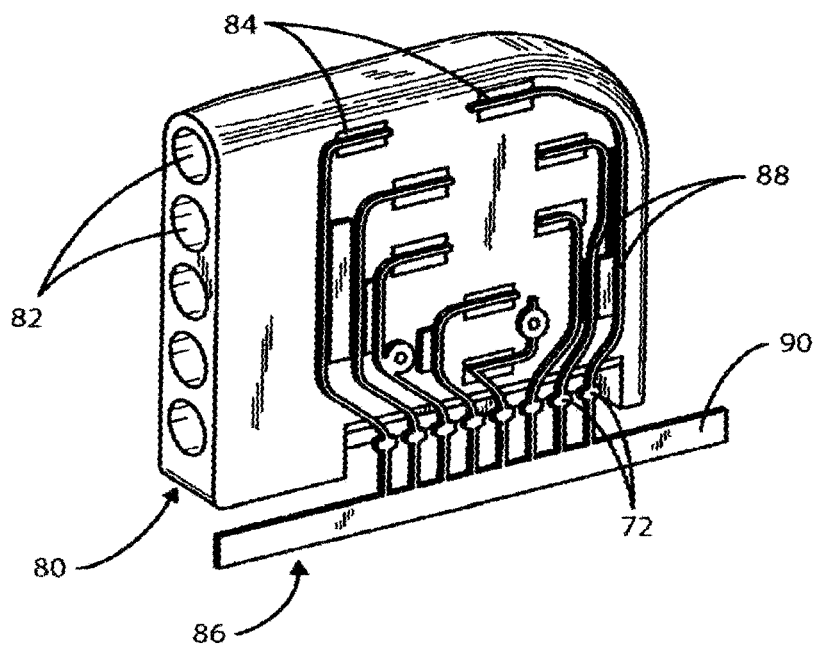
Figure 8:
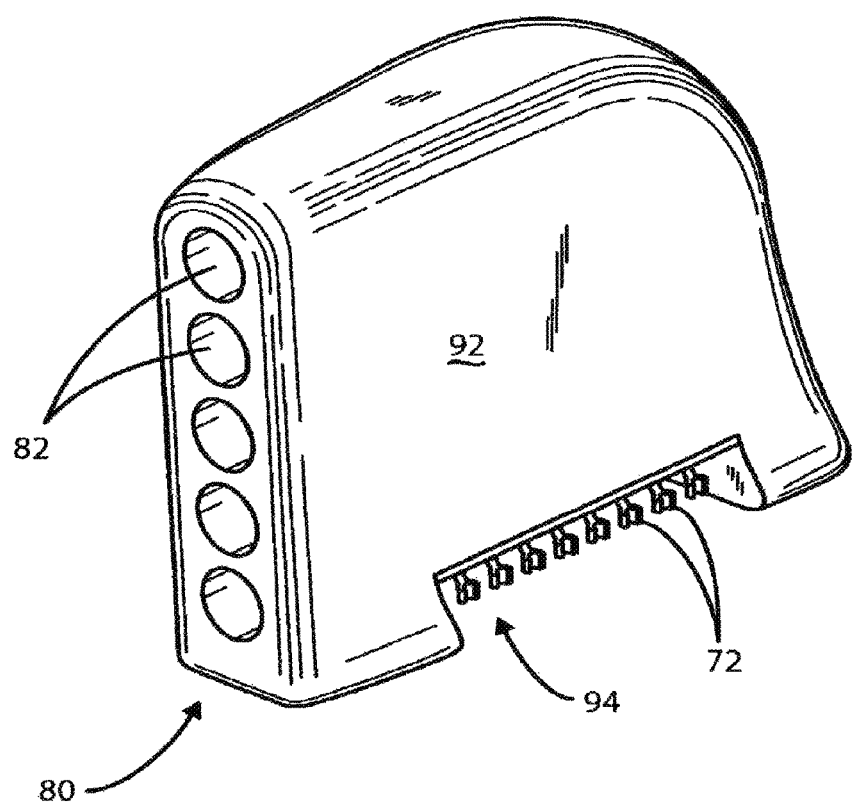

FIGS. 6-8 depict an alternative embodiment utilizing an inline external connector configuration including a pre-molded header module 80 having an array of inline external connection openings as at 82 adapted to receive external leads (not shown) in the usual well known manner. An array of possible side co-planar terminals or block connection sites as at 84 are provided and these are addressed by a pre-formed flex conductor system or harness 86 containing an array of leads or traces as at 88 not unlike those previously discussed and connected for manufacturing and assembly purposes by one or more stabilizing members as at 90, as shown in FIG. 7. In FIG. 7, the free ends of the traces 88 are shown in place on the side of module 80 and connected to the sites 84. Here, as in the case of the embodiment earlier described, connection is readily achieved by an assembler. These traces also are provided with spade connectors 72.

Figure 9:
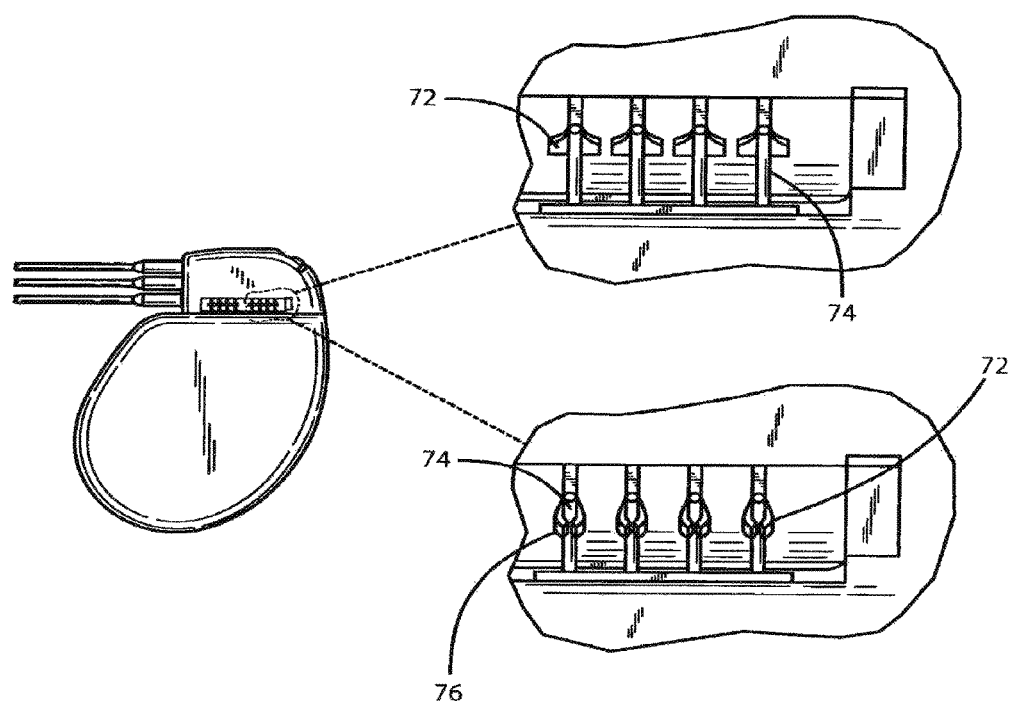
FIG. 9 shows an assembled device with parts cut away exposing the connection and greatly enlarged fragment views of a typical connection mode in accordance with the assembly of the header of the invention onto the hermetically sealed implantable unit.

FIG. 8 depicts the modular header 80 after the application of an overlayer 92 of medical grade polymer on the connection side which seals in the conductors 88 leaving only the array of terminal spade connectors 72 conveniently configured in an inline arrangement corresponding feed-through terminal pins 74 as depicted in FIG. 9 in the manner previously described.

Note that the remaining recess volume 75 in FIGS. 5A and 5B and 94 in FIG. 8 is quite small in relation to the size of the header module 40 or 80, such that the amount of backfilling after final connection to fill out and streamline the structure remains relatively minor.

The embodiments, once assembled, can easily be tested as by plugging the header module into a test stand and attaching any desired external leads. The use of the harness in combination with predetermined separate paths for the conductors precludes shorts and eliminates the need for using insulated conductors.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of fabricating a modular header for providing electrical connections between an array of feed-through pins extending through a wall of a hermetically sealed enclosure of an implantable medical device and lead connector receptacles within a modular header assembled to said device comprising:
    providing a pre-formed molded header module having paths therein to accept and incorporate a set of flexible conductive traces and connector blocks;
    providing a set of four or more interconnected flexible conductors each having a free end and a fixed end, the fixed end of each flexible conductor being connected to a removable common element shared by all the flexible conductors, and assembling said set of conductors into said recesses by said pre-formed molded header module attaching the free ends thereof to corresponding connector blocks provided in said molded header module;
    performing an over-molding operation to incorporate and hermetically seal said conductors into said header structure; and
    removing the common element such that a linear array of the four or more connectors are defined at the fixed ends by the removal of the common element.

2. The method of claim 1, wherein the linear array of connectors are configured and positioned to match and mate with the array of feed-through pins when said header is assembled to a compatible corresponding hermetically sealed enclosure.

3. The method of claim 2, wherein the removable common element is elongate and wherein the fixed ends of the flexible conductors are connected to a top surface of the elongate removable common element.

4. The method of claim 1, further including assembling said header module to said hermetically sealed enclosure and connecting said flexible conductors to said feed-through pins.

5. The method of claim 4, further including backfilling any open interface volume between said header module and said hermetically sealed enclosure after connecting said flexible conductors to said feed-through pins.

6. The method of claim 1, wherein the paths include a first channel, second channel, a third channel, and a fourth channel.

7. The method of claim 6, wherein the flexible conductors include a first conductor including a first connection terminal, a second conductor including a second connection terminal, a third conductor including a third connection terminal, and a fourth conductor including a fourth connection terminal, the flexible conductors define a pre-formed alignment wherein the first conductor is disposed in the first channel, the second conductor is disposed in the second channel, the third conductor is disposed in the third channel, and the fourth conductor is disposed in the fourth channel.

8. The method of claim 7, wherein the first, second, third, and fourth conductors are physically coupled to a top, upper surface of the removable common element that defines a longitudinal axis, the first, second, third, and fourth conductors are in spaced alignment along the longitudinal axis, and the first, second, third, and fourth conductors each extend in a direction perpendicular to the longitudinal axis.

9. The method of claim 1 comprising the further step of assembling said header module to said hermetically sealed enclosure and connecting said header connectors to said feed-through pins.

10. The method of claim 1 further comprising the step of backfilling any open interface volume between said header module and said hermetically sealed enclosure after connecting said header connectors to said feed-through pins.

* * * * *